US00PP35148P2

(12) United States Plant Patent
Yencho et al.

(10) Patent No.: US PP35,148 P2
(45) Date of Patent: May 2, 2023

(54) SWEETPOTATO VINE NAMED 'NCORNSP-029SCBC'

(50) Latin Name: ***Ipomoea batatas* (L.) Lam.**
Varietal Denomination: NCORNSCP-029SCBC

(71) Applicant: North Carolina State University, Raleigh, NC (US)

(72) Inventors: George Craig Yencho, Raleigh, NC (US); Kenneth Vincent Pecota, Raleigh, NC (US); Christopher Heim, Morrisville, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/803,766

(22) Filed: Nov. 15, 2022

(51) Int. Cl.
*A01H 5/12* (2018.01)
*A01H 6/00* (2018.01)

(52) U.S. Cl.
USPC ..... Plt./258

(58) Field of Classification Search
USPC ..... Plt./258
See application file for complete search history.

*Primary Examiner* — Susan McCormick Ewoldt
(74) *Attorney, Agent, or Firm* — Myers Bigel, P.A.

(57) ABSTRACT

'NCORNSP-029SCBC' is a vigorous, highly-twining, climbing variety of *Ipomoea batatas* producing many shoots. It is distinguishable from other ornamental sweetpotato cultivars by its palmate, deeply lobed leaves with 3-5 lobes, an aggressive climbing habit, and heavily branched architecture. The purple leaves, long internodes, and the plant architecture, which promotes good plant production in the greenhouse for wholesale distributors, distinguishes 'NCORNSP-029SCBC' amongst the current ornamental sweetpotatoes in the marketplace. 'NCORNSP-029SCBC' exhibits very good vigor and is very well branched. 'NCORNSP-029SCBC' is suitable for use in vertical landscape or container plantings.

6 Drawing Sheets

Latin name of the genus and species: The Latin name of the novel, ornamental plant variety disclosed herein is *Ipomoea batatas* (L.) Lam.

Variety denomination: The inventive cultivar of *Ipomoea batatas* disclosed herein has been given the varietal denomination 'NCORNSP-029SCBC'.

BACKGROUND OF THE INVENTION

*Ipomoea batatas* is a member of the morning glory family Convolvulaceae. This species is grown worldwide and it exhibits a wide range of plant forms and colors. The cultivated members of *Ipomoea batatas* grown by farmers worldwide are commonly produced for consumption of their nutritious, enlarged storage roots. These types typically produce a fast growing green vine that has a wide variety of leaf shapes ranging from palmate and deeply lobed, to cordate or triangular shaped leaves with no lobes.

Like their edible forms, *Ipomoea batatas* ornamental sweetpotato plants are a heat-loving, drought-tolerant, perennial vine typically grown as an annual. However, ornamental sweetpotato plants are distinguished from the edible cultivated forms in that they often do not produce attractive, enlarged storage roots suitable for human consumption. Instead, they possess unique foliage colors, leaf shapes, and growth habits, which have significant value in the ornamental marketplace.

Ornamental sweetpotatoes are desirable in the landscape and ornamental industries because their foliage comes in a wide variety of colors (e.g., pale yellow to dark purple with some exhibiting temporal and individual leaf color variegation patterns) and plant shapes (e.g., mounded and very compact to prostrate and highly spreading). They can be grown in a potted plant and/or mixed planting format, and they have the ability to cover a large space or hang over walls and decorative pots creating brightly colored and textured backdrops in gardens and patios. Most ornamental sweetpotatoes grow and last the entire growing season and they require little maintenance. Moreover, these plants have few insect or disease problems.

To meet the growing horticultural demand for ornamental sweetpotatoes, it is desirable to produce new cultivars of ornamental sweetpotato with new or improved foliage colors, variegation patterns, leaf shapes, and plant architectures. In addition, it would be advantageous to develop some cultivars of ornamental sweetpotato exhibiting a more compact growth that do not out-compete other species in mixed containers, and others exhibiting varied architectures and vigor to address ever evolving ornamental garden and landscape needs.

'NCORNSP-029SCBC' was bred to meet the demand for new ornamental sweetpotatoes. 'NCORNSP-029SCBC' is a vigorous, highly-twining, climbing variety producing many shoots. It is distinguishable from other ornamental sweetpotato cultivars by its palmate, deeply lobed leaves with 3-5 lobes, an aggressive climbing habit, and heavily branched architecture. The purple leaves, long internodes, and plant architecture, which promotes good plant production in the greenhouse for wholesale distributors, distinguishes 'NCORNSP-029SCBC' amongst the current ornamental sweetpotatoes in the marketplace. 'NCORNSP-029SCBC' exhibits very good vigor and is very well branched. In greenhouse and field trials conducted since 2018 by the breeding program and industry collaborators 'NCORNSP-029SCBC' has been shown to be of similar vigor to *Ipomoea batatas* 'Margarita' (unpatented) and 'Blackie' (unpatented)

and is suitable for use in vertical landscape or container plantings. The production of flowers by 'NCORNSP-029SCBC' is sporadic under short day conditions.

Lineage. 'NCORNSP-029SCBC' (breeding designation NC9824-096ORN) originated from hand-pollinated seed from the proprietary *Ipomoea batatas* breeding lines NCN29ORN (the female parent; not patented) and NC6879-008ORN (the male parent; not patented). Botanical seed was harvested from ornamental lines grafted onto a flower-inducing *Ipomoea setosa* sweetpotato line in greenhouses between October 2016 and April 2017 in Raleigh, N.C. NCN29ORN resulted from open-pollinated seed harvested from the proprietary *Ipomoea batatas* breeding line NC775-1ORN (the female parent; not patented). NC6879-008ORN resulted from open pollinated seed collected from NC4626-002ORN (the female parent; NCORNSP-015SCPI; U.S. Plant Pat. No. 23,613). Botanical seed from this family were planted in the greenhouse in December 2017. The first cycle of selection on the population was exercised at the seedling tray stage and each survivor was transferred to a single 6-inch pot, which was then maintained in the greenhouse. Cuttings (2 each) were taken from the plants in April and planted in the field as unreplicated 2-plant plots, during mid-June 2018. The single, individual plant now known as 'NCORNSP-029SCBC' was selected Sep. 25, 2018, because of its combination of exceptional features, and it has been propagated asexually since that time.

Asexual Reproduction. Since its selection, *Ipomoea batatas* 'NCORNSP-029SCBC' has been asexually reproduced in Raleigh, N.C. predominantly by vegetative propagation of vine cuttings. Successively, there have been four cycles of vegetative propagation, one cycle of tissue culture micropropagation, and multiple vegetative propagation cycles to increase plant numbers. Asexual reproduction of 'NCORNSP-029SCBC' by cuttings has shown that the unique features of the new cultivar are stable and the plant reproduces true to type in successive generations.

SUMMARY OF THE INVENTION

'NCORNSP-029SCBC' was bred to meet the demand for new ornamental sweetpotatoes. 'NCORNSP-029SCBC' is a vigorous, highly-twining, climbing variety producing many shoots. It is distinguishable from other ornamental sweetpotato cultivars by its palmate, deeply lobed leaves with 3-5 lobes, an aggressive climbing habit, and heavily branched architecture. Its purple leaves, long internodes, and the plant architecture, which promotes good plant production in the greenhouse for wholesale distributors, distinguishes 'NCORNSP-029SCBC' amongst the current ornamental sweetpotatoes in the marketplace. 'NCORNSP-029SCBC' exhibits very good vigor and is very well branched. In greenhouse and field trials conducted since 2018 by the breeding program and industry collaborators 'NCORNSP-029SCBC' has been shown to be of similar vigor to *Ipomoea batatas* 'Margarita' and 'Blackie' and is suitable for use in vertical landscape or container plantings. The production of flowers by 'NCORNSP-029SCBC' is sporadic under short day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which more accurately describe the colors of the new *Ipomoea batatas*.

DETAILED BOTANICAL DESCRIPTION OF THE NEW VARIETY

Figure 1:
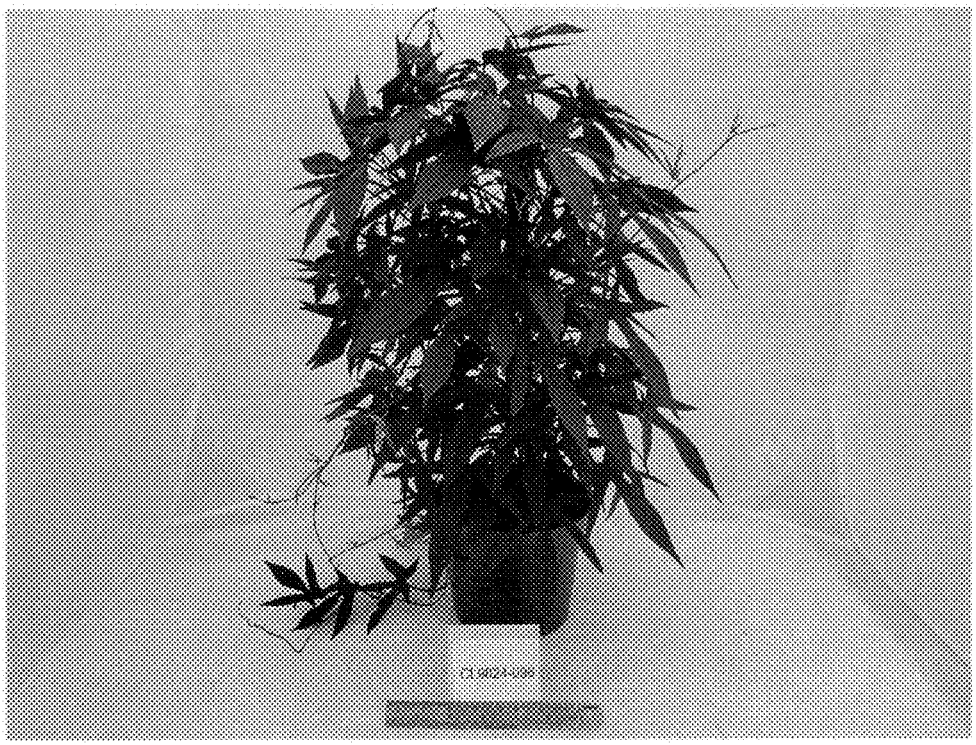
FIG. 1 is a color photograph of a typical specimen of greenhouse grown *Ipomoea batatas* 'NCORNSP-029SCBC' in a 6-inch pot from the side, 50 days after planting.
Figure 2:
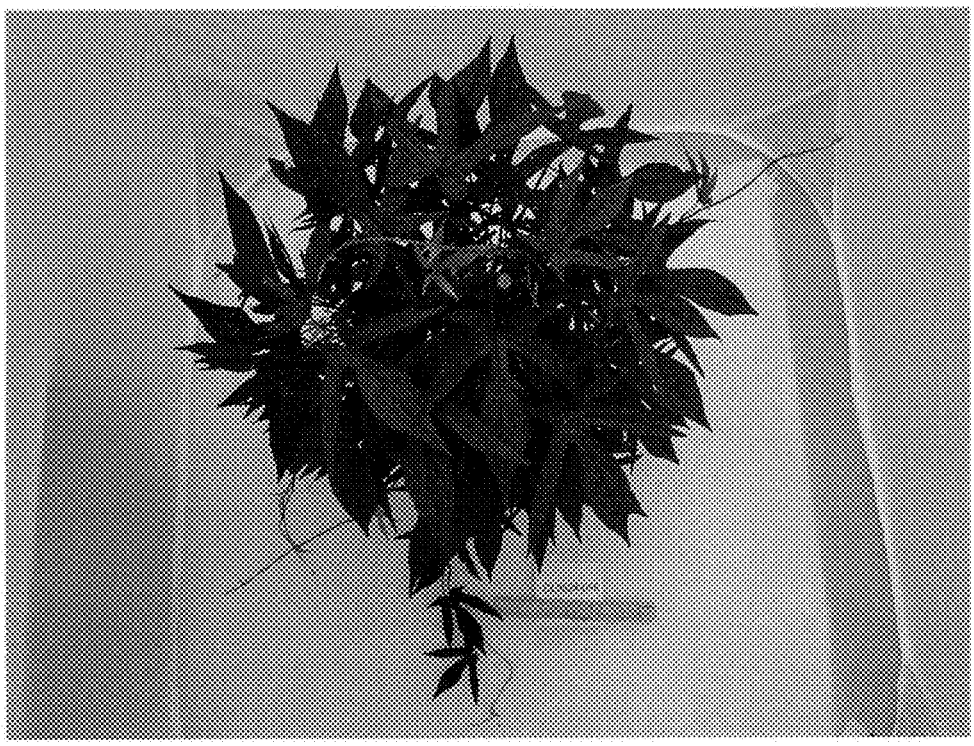
FIG. 2 is a color photograph of a typical specimen of greenhouse grown *Ipomoea batatas* 'NCORNSP-029SCBC' in a 6-inch pot from the top, 50 days after planting.
Figure 3:
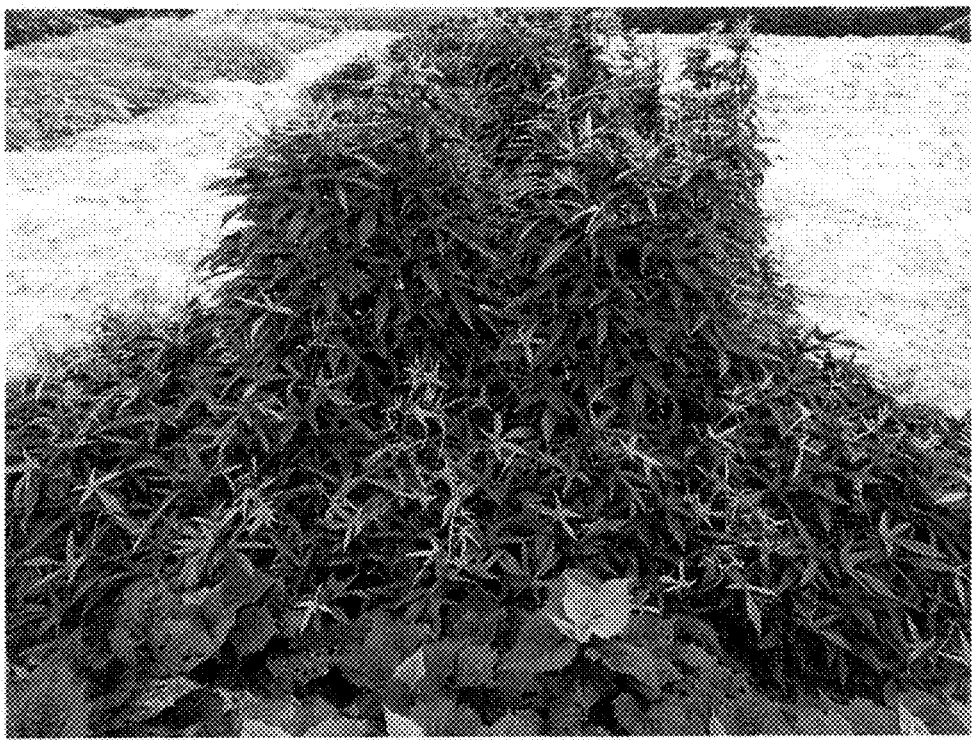
FIG. 3 is a color photograph of a typical specimen of *Ipomoea batatas* 'NCORNSP-029SCBC' from the side in the field, 75 days after planting.
Figure 4:
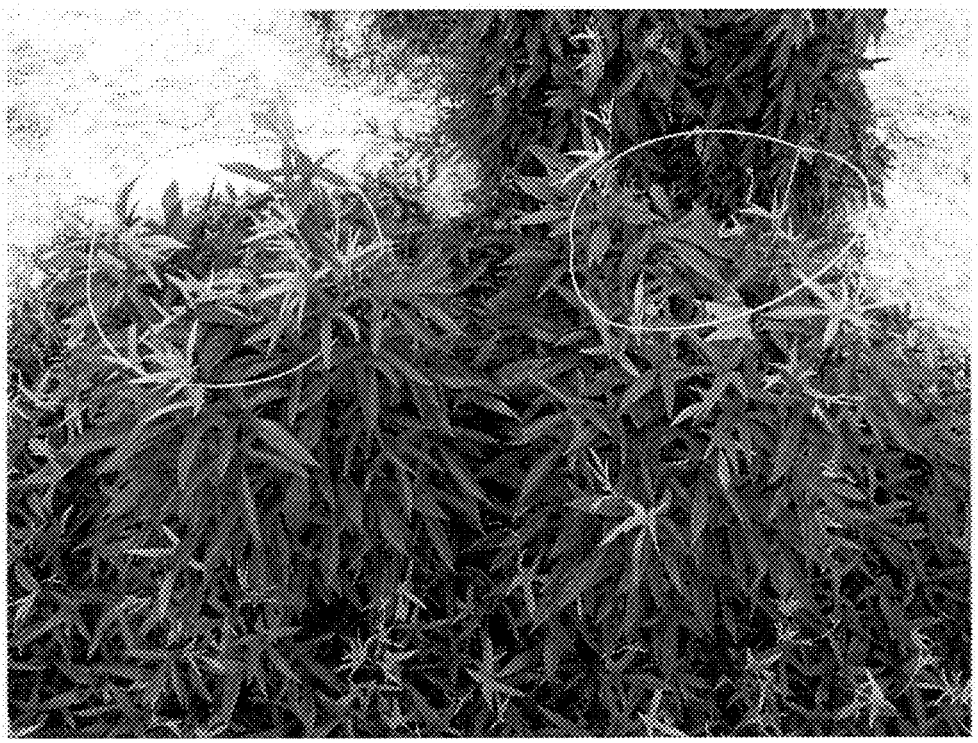
FIG. 4 is a color photograph of a typical specimen of *Ipomoea batatas* 'NCORNSP-029SCBC' from the top in the field, 75 days after planting.
Figure 5:
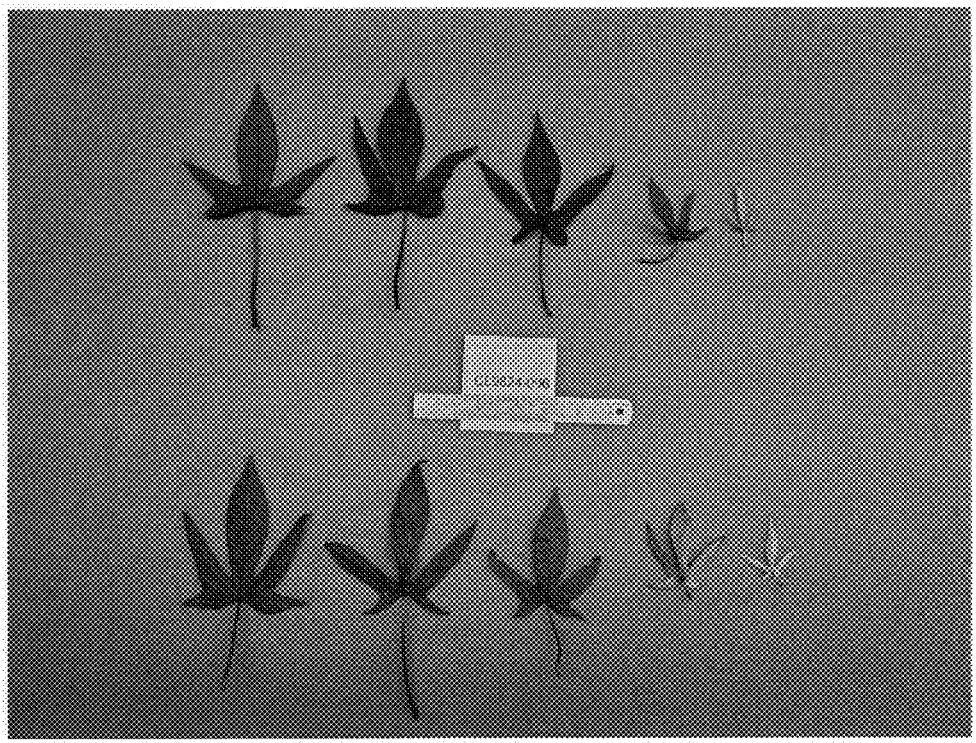
FIG. 5 is a color photograph showing the upper (top) and lower (bottom) surfaces of mature leaves produced by greenhouse grown *Ipomoea batatas* 'NCORNSP-029SCBC', 50 days after planting.

The following is a detailed description of the botanical characteristics of a new and distinct cultivar of *Ipomoea batatas* plant known by the cultivar name 'NCORNSP-029SCBC'. All colors cited herein refer to The Royal Horticulture Society Colour Chart designations (The Royal Horticultural Society, London, 1995, $4^{th}$ ed.) except where general terms of ordinary dictionary significance are used. Plant descriptions are based on the standardized international sweetpotato descriptors established jointly by the International Potato Center (CIP), Lima, Peru; The Asian Vegetable Research and Development Center (AVRDC), Taipei, Taiwan; and the International Board for Plant Genetics Resources (IBPGR), Rome, Italy (CIP, AVRDC, IBPGR. 1991. Descriptors for Sweet Potato. Huaman, Z., editor. International Board for Plant Genetic Resources, Rome, Italy, 134 pp.). Where dimensions, sizes, colors, and other characteristics are given, it is to be understood that such characteristics are approximations or averages set forth as accurately as practicable.

The descriptions reported herein are from a group of 50-day-old specimens grown individually in six-inch azalea pots. The plants were grown in Raleigh, N.C., under commercial practice in a glass-covered greenhouse, where, during the fall, day and night temperatures range between 30-40° C. and 22-26° C., respectively. After rooting, plants were treated with 200 ppm 20-10-20 fertilizer weekly. Plant histories were taken in October 2021 in Raleigh, N.C. *Ipomoea batatas* 'NCORNSP-029SCBC' has not been observed under all possible environmental conditions; therefore, the phenotype may vary under different environmental conditions such as season, temperature, light intensity, day length, cultural conditions, and the like, without however, any variance in the genotype.

Classification.

*Botanical name.*—*Ipomoea batatas* (L.) Lam.

*Common name.*—Ornamental Sweetpotato.

*Variety name.*—'NCORNSP-029SCBC'.

Growth conditions: *Ipomoea batatas* 'NCORNSP-029SCBC' has very good vigor and a rapid growth rate. In locations with mild winter conditions, *Ipomoea batatas* 'NCORNSP-029SCBC' will grow perennially; otherwise, it is an annual plant. Similar to other cultivated sweetpotatoes, wind or rain rarely cause much damage to 'NCORNSP-029SCBC', but if damage does occur, the plant drops the damaged leaves and grows new shoots at nodes where the leaves were lost. Under low light levels in a greenhouse, 'NCORNSP-029SCBC' can develop intumescence, which will remain on the affected foliage, but will be outgrown with new foliage.

Aboveground structure and coloration: FIGS. 1, 2, 3, 4 and 5 show the shape and coloration of a typical specimen of *Ipomoea batatas* 'NCORNSP-029SCBC'. Color may vary somewhat due to temperature and nutrient stress. Overall, this cultivar is a vigorous, highly-twining, climbing herbaceous plant that has an average height of about 42.1 cm and an average area spread of about 41.3 cm. The growth habit of this plant is to grow upright with shoots climbing upward and outward.

Branches:

*Branching habit.*—Freely-branching with about 10-11 primary lateral branches coming off the stem. Very dense foliage and no pinching is required to stimulate branching. Branch texture is smooth and glabrous.

*Vegetative lateral branching.*—Length: about 64.5 cm. Diameter: about 0.2 cm. Internodes are moderately long with an average length of about 6.9 cm.

*Secondary lateral shoots.*—No measurable secondary lateral shoots formed on the rated plants.

*Stem.*—Round and smooth with an upward, very strong, slightly flexible, non-brittle strength. Color: Greyed-purple (RHS N186C-D).

*Adventitious roots.*—Absent at nodes.

Foliage: Leaves are alternate and tend to slightly spiral around the stem. They are simple and heavily divided into 3-5 lobes. Leaf shape is somewhat variable as is size. (see FIG. 5).

*Quantity.*—Heavily foliated, with about 17.5 leaves per lateral branch.

*Mature leaf length.*—About 9.6 cm.

*Mature leaf width.*—About 11.7 cm.

*Leaf margin.*—Entire.

*Leaf apex.*—Acuminate.

*Leaf base.*—Cordate to auriculate.

*Leaf texture.*—Glabrous texture and matte finish.

*Venation.*—Arcuate to cross-venulate.

*Color.*—Leaves are greyed-purple (RHS N187A) and range within that palate as they mature. See also Table 1.

*Petiole.*—Petioles are held slightly upward and curve outward. Leaf petiole has a smooth glabrous texture. Length: about 8.3 cm. Diameter: about 0.1 cm. Color: Greyed-purple (RHS N186C-D).

TABLE 1

Leaf color of *Ipomoea batatas* 'NCORNSP-029SCBC'.

| Leaf Structure | Upper Surface | Lower Surface |
|---|---|---|
| Mature Leaf | Greyed-Purple (RHS N187A) | Greyed-Purple (RHS N186C) |
| Young Leaf | Yellow-Green (RHS 144B) | Yellow-Green (RHS 144D) |

TABLE 1-continued

Leaf color of *Ipomoea batatas* 'NCORNSP-029SCBC'.

| Leaf Structure | Upper Surface | Lower Surface |
|---|---|---|
| Vein- mature leaf | Greyed-Purple (RHS N186C) | Purple (RHS N79B) |
| Vein -young leaf | Yellow-Green (RHS 144A) | Yellow-Green (RHS 144D) |

Inflorescence: The production of flowers by 'NCORNSP-029SCBC' is very sporadic and mostly observed under stressful conditions (e.g., drought, nutrient stress, cloudy weather). Shorter day lengths enhance flowering, but the precise photoperiod for flower induction is currently unknown. Solitary, regular funnel-form flowers arising from leaf axils on secondary lateral branches are formed. Peduncles are purple (RHS N79C). Peduncle length: about 4.3 cm, peduncle width: about 0.1 cm. Flower buds are purple (RHS 76B-76D) and elliptic. Limb color: purple (RHS 76C) on the outer surface and purple (RHS 77D) on the inner surface. The outer throat color begins purple (RHS 76C) and gradually lightens towards the limb. The limb is pentagonal with no fragrance. The flower averages five sepals. The outer sepals are shorter than the inner sepals. Average outer sepal length: about 1.0 cm, average outer sepal width: about 0.3 cm, average inner sepal length: about 1.2 cm, average inner sepal width: about 0.5 cm. The sepals are elliptic with an acute apex and smooth margins and are purple (RHS N79A) in color. A single pistil consists of one style and one stigma about 2.5 cm in length. Stigma and style are both cream (RHS 157A). The stigma is slightly exerted relative to the stamens. The flower averages five stamens. Pollen color: cream (RHS 155A). Pollen is profuse. Fruit has not been observed under normal greenhouse conditions.

Figure 6:
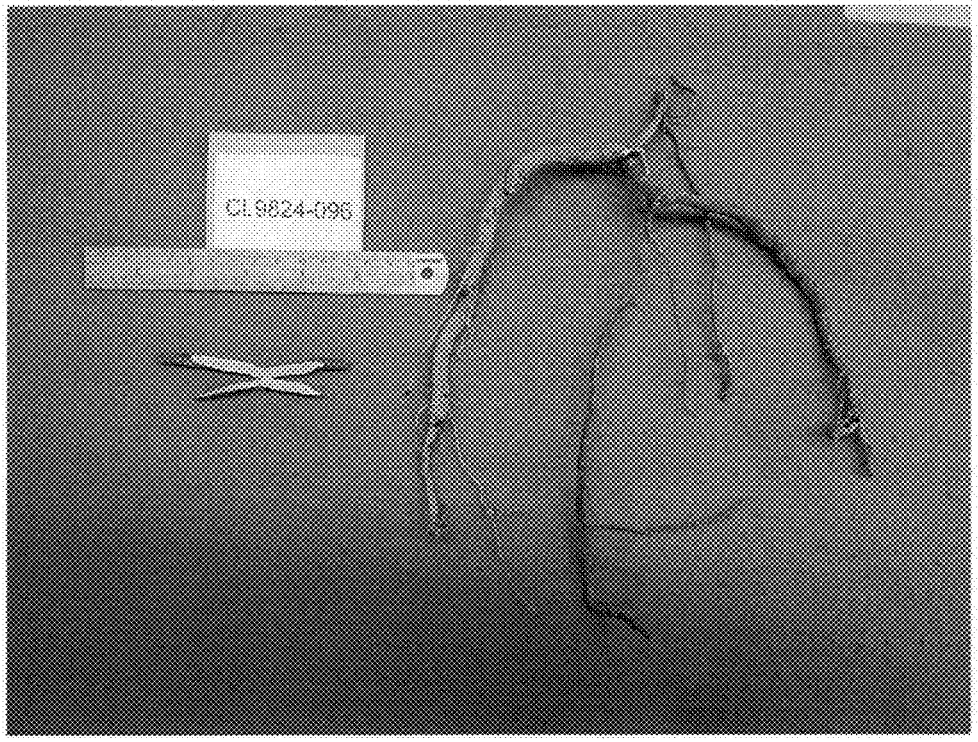
FIG. 6 is a color photograph showing the storage roots produced by *Ipomoea batatas* 'NCORNSP-029SCBC' in the field, 134 days after planting.

Storage root coloration: *Ipomoea batatas* 'NCORNSP-029SCBC' forms no, to small, underground storage roots that are typically malformed and do not meet USDA Sweetpotato Storage Root Grade Standards (see FIG. 6). Fibrous roots are typically cream (RHS 155B). Storage roots that are formed possess purple (RHS N77B) skin with a yellow (RHS 11D) primary flesh color and yellow-orange (RHS 16D) secondary flesh color.

Disease or pest resistance: 'NCORNSP-029SCBC' is susceptible to whiteflies and thrips in a greenhouse environment. 'NCORNSP-029SCBC' is susceptible to damage by Japanese beetles under outdoor conditions. The susceptibility of 'NCORNSP-029SCBC' to other known insects and pathogens of sweetpotato is unknown. Under low light conditions, slight edema may occur.

Comparison with other *Ipomoea batatas* cultivars: 'NCORNSP-029SCBC' is distinct based on plant architecture and leaf shape. Of the common cultivars of ornamental sweetpotato, 'NCORNSP-029SCBC' is best compared with the 'Balsotowac' (U.S. Plant Pat. No. 29,511) and 'NCORNSP-024SCRI' (U.S. Plant Pat. No. 31,837) cultivars (Table 2). Like both 'Balsotowac' and 'NCORNSP-024SCRI', 'NCORNSP-029SCBC' has greyed-purple to purple leaves. However, the branching of 'NCORNSP-029SCBC' is significantly denser than either 'Balsotowac' or 'NCORNSP-024SCRI'. Additionally, 'NCORNSP-029SCBC' has a climbing architecture, while 'NCORNSP-024SCRI' is a compact, non-twining plant. The abundance of branching and degree of twining in 'NCORNSP-029SCBC' is also significantly higher than that in 'Balsotowac', leading to a more full and consistent climbing architecture. The lobes of 'NCORNSP-029SCBC' are deeper than 'NCORNSP-024SCRI', and 'Balsotowac' has no lateral lobes.

'NCORNSP-029SCBC' is distinct from its parents, NCN29ORN and NC6879-008ORN, by its leaf lobing and color. 'NCORNSP-029SCBC' has deeper lateral lobes than either NCN29ORN or NC6879-008ORN. Additionally, both NCN29-ORN and NC6879-008ORN consistently have leaves with 3 lobes, while 'NCORNSP-029SCBC' has 3-5 lobes. 'NCORNSP-029SCBC' has a darker greyed-purple color than NC6879-008ORN (which has green undertones), and NCN29ORN has yellow-green leaves.

TABLE 2

Comparison of 'NCORNSP-029SCBC' with other *Ipomoea batatas* cultivars.

| Characteristic | 'NCORNSP-029SCBC' | 'Balsotowac' | 'NCORNSP-024SCRI' |
|---|---|---|---|
| Plant Habit | Climbing, highly twining habit | Slightly climbing, slightly twining, trailing habit | Compact, semi-erect and mounding habit |

TABLE 2-continued

Comparison of 'NCORNSP-029SCBC' with other *Ipomoea batatas* cultivars.

| Characteristic | 'NCORNSP-029SCBC' | 'Balsotowac' | 'NCORNSP-024SCRI' |
|---|---|---|---|
| Average Leaf Length and Width | Length: 9.6 cm Width: 11.7cm | Length: 9.7 cm Width: 9.2 cm | Length: 11.6 cm Width: 14.2 cm |
| Foliage Color | Greyed-purple (RHS N187A) | Greyed-purple (RHS N186B-C) | Greyed-purple (RHS N186A) |
| Leaf Shape | Deeply lobed, 3-5 lobes. Entire with an acuminate apex and a cordate to auriculate base. | Unlobed. Entire with an apiculate apex and cordate base. | Moderately lobed, 3-5 lobes. Entire with an apiculate to aristate apex and a auriculate base. |

We claim:

1. A new and distinct cultivar of *Ipomoea batatas* plant named 'NCORNSP-029SCBC', substantially as illustrated and described herein.

* * * * *